US009839726B2

(12) United States Patent
Ehlert

(10) Patent No.: US 9,839,726 B2
(45) Date of Patent: Dec. 12, 2017

(54) THORACIC DRAINAGE DEVICE HAVING REDUCED COUNTER-PRESSURE

(75) Inventor: Hilmar Ehlert, Hergiswil (CH)

(73) Assignee: MEDELA HOLDING AG, Baar (CH)

( * ) Notice: Subject to any disclaimer, the term of this patent is extended or adjusted under 35 U.S.C. 154(b) by 1012 days.

(21) Appl. No.: 14/128,041

(22) PCT Filed: Jul. 5, 2012

(86) PCT No.: PCT/CH2012/000156
§ 371 (c)(1),
(2), (4) Date: Mar. 18, 2014

(87) PCT Pub. No.: WO2013/003970
PCT Pub. Date: Jan. 10, 2013

(65) Prior Publication Data
US 2014/0213992 A1 Jul. 31, 2014

(30) Foreign Application Priority Data

Jul. 7, 2011 (CH) ..................................... 1141/11

(51) Int. Cl.
*A61M 1/00* (2006.01)
*A61B 1/015* (2006.01)

(52) U.S. Cl.
CPC .......... *A61M 1/0023* (2013.01); *A61B 1/015* (2013.01); *A61M 2205/3331* (2013.01); *A61M 2205/50* (2013.01); *A61M 2210/101* (2013.01)

(58) Field of Classification Search
CPC ........ A61M 1/0023; A61M 2205/3331; A61M 2205/50; A61M 2210/101; A61B 1/015
(Continued)

(56) References Cited

U.S. PATENT DOCUMENTS

| 4,439,190 A | 3/1984 | Protzmann et al. |
| 4,654,029 A | 3/1987 | D'Antonio |

(Continued)

FOREIGN PATENT DOCUMENTS

| WO | WO-9910024 A1 | 3/1999 |
| WO | WO-2003/103747 A1 | 12/2003 |

(Continued)

OTHER PUBLICATIONS

Written Opinion of the International Searching Authority for Application No. PCT/CH2012/000156, dated Jul. 11, 2012.
(Continued)

*Primary Examiner* — Tatyana Zalukaeva
*Assistant Examiner* — Andrew J Mensh
(74) *Attorney, Agent, or Firm* — Marshall, Gerstein & Borun LLP

(57) ABSTRACT

A device for thoracic drainage comprises a container connector for a secretion collection container (3), which can be connected to the pleural cavity of a patient, and a venting device (10) for releasing air from the secretion collection container in passive operation. In order to keep the counterpressure as low as possible during the air release and thus make it easier to force air out of the pleural cavity (1) of a patient, the venting device has a controllable vent valve (12). For this purpose, a control device (7) determines the pressure in the secretion collection container by reading out a pressure sensor (11) and controls the valve to release air from the secretion collection container when the determined pressure exceeds a threshold value. The device can optionally also be operated actively by way of a vacuum connector (25). An ancillary line (2') permits monitoring of the drainage line (2).

24 Claims, 3 Drawing Sheets

(58) Field of Classification Search
USPC .......................................................... 604/317
See application file for complete search history.

(56) References Cited

U.S. PATENT DOCUMENTS

| | | |
|---|---|---|
| 5,931,821 A | 8/1999 | Weilbacher et al. |
| 2004/0260255 A1* | 12/2004 | Charlez .............. A61M 1/0013 604/317 |
| 2006/0122558 A1 | 6/2006 | Sherman et al. |

FOREIGN PATENT DOCUMENTS

| | | |
|---|---|---|
| WO | WO-2005/061025 A1 | 7/2005 |
| WO | WO-2007/128156 A2 | 11/2007 |
| WO | WO-2008/141471 A1 | 11/2008 |

OTHER PUBLICATIONS

International Search Report for Application No. PCT/CH2012/000156, dated Jul. 11, 2012.

* cited by examiner

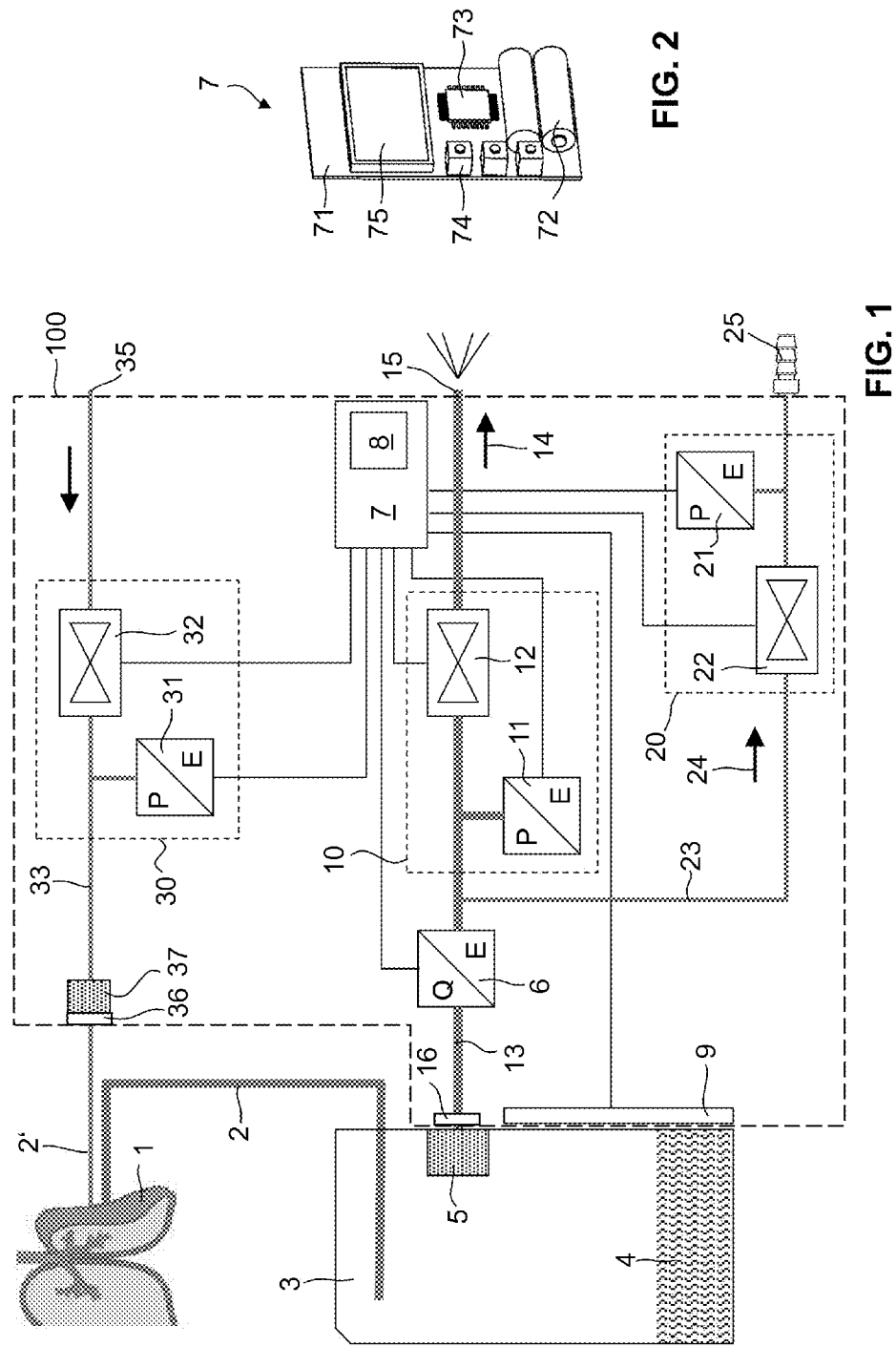

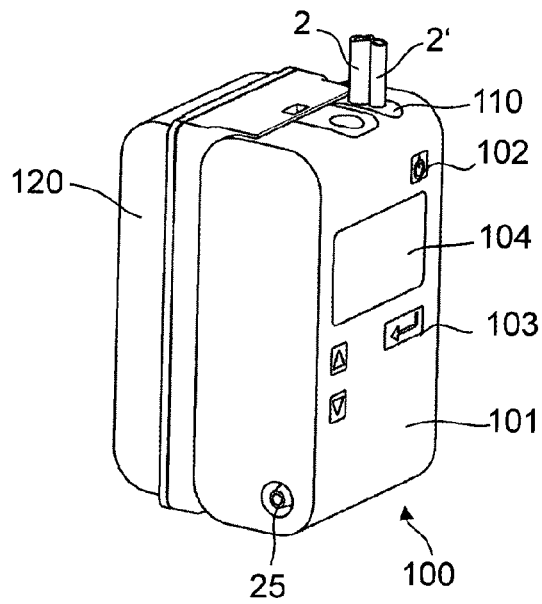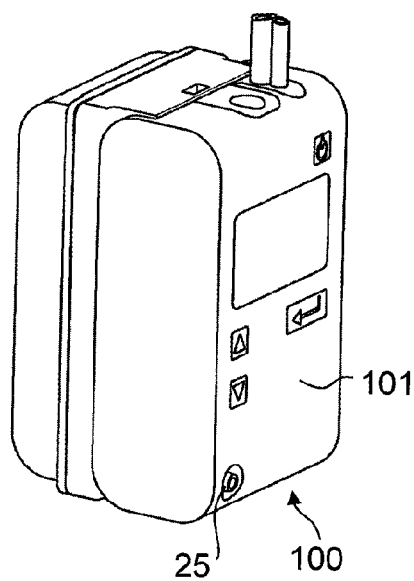
FIG. 3   FIG. 4
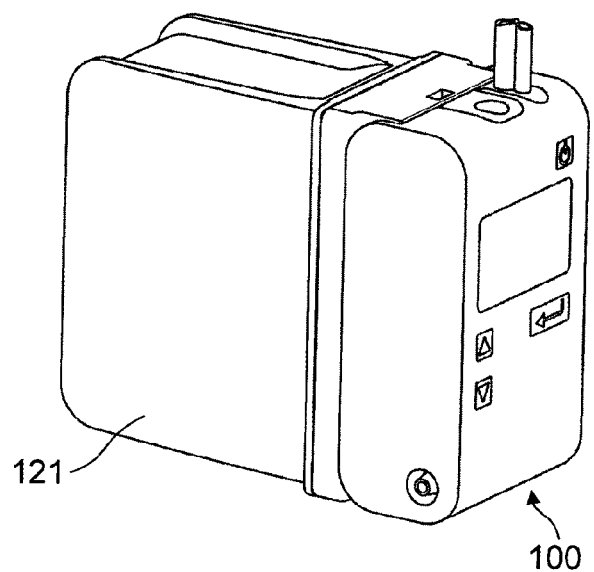
FIG. 5

THORACIC DRAINAGE DEVICE HAVING REDUCED COUNTER-PRESSURE

CROSS-REFERENCE TO RELATED APPLICATION

The present application is the United States national phase of International Patent Application No. PCT/CH2012/000156, filed Jul. 5, 2012, which application claims priority of Switzerland Application No. 1141/11 filed Jul. 7, 2011. The priority application, CH 1141/11, is incorporated herein by reference.

FIELD OF THE DISCLOSURE

Technical Field

The present invention relates to a device for thoracic drainage and to a corresponding method and computer program.

Prior Art

In patients with defects on the chest wall or lung surface, it is possible for air and secretions to collect in the pleural cavity. This is often treated by carrying out thoracic drainage (pleural drainage), in which air and secretions are removed from the pleural cavity via a drainage catheter. A distinction is made between active systems, in which a vacuum is actively applied to the pleural cavity, and passive systems, which operate without vacuum assistance.

In both types of systems, the drainage catheter is in most cases connected to a secretion collection container by way of a drainage line, in order to separate liquid secretions. The secretion collection container is in most cases adjoined by a water seal, which permits release of air from the secretion collection container but prevents air from passing through the secretion collection container, the drainage line and the drainage catheter back into the pleural cavity. In active drainage systems, a vacuum source is also then connected to the water seal. A thoracic drainage system of this kind is disclosed in WO 2003/103747, for example.

For active thoracic drainage systems, it has already been proposed in the prior art to do without a water seal or to replace the water seal by a mechanical one-way valve in order to make the thoracic drainage system easier to handle and, in particular, give it a portable design. Examples of active thoracic drainage systems of this kind are found in WO 99/10024, in WO 2007/128156 and in WO 2008/141471.

A water seal consists of an airtight container which is filled partially with liquid, in most cases water, and into which two pipes protrude from above, which pipes form a first and a second connector of the water seal. The first pipe protrudes to a position below the surface of the water, whereas the second pipe ends above the surface of the water. Air can enter the water seal through the first pipe, pass through the water in the form of air bubbles and escape through the second pipe. In the reverse direction, the water ensures that air entering through the second pipe cannot pass into the first pipe. The water seal works to this extent as a one-way valve (nonreturn valve).

To ensure that air can pass through the first pipe and through the water, the air must be at a certain minimum pressure. This is because the air first of all has to displace the water column in the lower end of the first pipe. The first pipe typically protrudes into the water by a distance of between one and a few centimeters, e.g. by 2 cm. Accordingly, the air entering the water seal through the first pipe must in this case have a positive minimum pressure of ca. 2 cm $H_2O$ (corresponding to 2 mbar or 0.2 kPa) in relation to the atmospheric pressure in order to pass through the water.

In passive thoracic drainage with a water seal, the patient has to apply this minimum pressure himself or herself in order to be able to force air out of the pleural cavity, e.g. by coughing. In such circumstances, the lung collapses to a certain degree. This is in most cases not beneficial to the healing process.

SUMMARY OF THE DISCLOSURE

In a first aspect of the present invention, it is therefore an object to provide a thoracic drainage device which, in passive operation, makes it easier for the patient to force air out of the pleural cavity.

A device for thoracic drainage is therefore proposed, comprising:

a connector (hereinafter designated as container connector) for a secretion collection container that is adapted to be connected to the pleural cavity; and a venting device for releasing air from the secretion collection container.

According to the invention, the venting device is characterized in that it comprises a controllable first valve. This controllable valve is also designated hereinafter as vent valve or air release valve.

The device can include the actual secretion collection container. However, the invention is also directed to the device without attached secretion collection container.

Since the venting device has a controllable valve, i.e. a valve that can change its operating state by means of suitable control signals without manual input, it is possible to keep the counterpressure very low during the air release. This can be achieved by the valve being selectively opened when the difference between the pressure in the secretion collection container and the outside pressure exceeds a defined first threshold value. This threshold value can be chosen as a very small positive value, e.g. a value of between 0.001 and 0.1 kPa, preferably of between 0.01 and 0.05 kPa. In this way, the valve opens as soon as air from the pleural cavity enters the secretion collection container, without the need to first of all overcome a relatively high counterpressure. In this way, the patient can more easily force out the air accumulated in the pleural cavity. As soon as the pressure falls back below a second threshold value, which can be the same as or less than the first threshold value, e.g. when the pressure difference is negative, the valve can be actively closed again in order to avoid air flowing back into the pleural cavity.

The vent valve is preferably controllable by electrical signals, but it can also be controlled by other types of signals, e.g. by optical signals, hydraulically or pneumatically. This also applies to all the other controllable valves mentioned below. Suitable controllable valves are known in large numbers from the prior art.

To be able to control the vent valve automatically, the device preferably comprises a first pressure sensor for determining the pressure in the secretion collection container, and an electronic control device (controller) which cooperates with this pressure sensor and which controls the vent valve according to the pressure measured. The first pressure sensor is also designated hereinbelow as a container pressure sensor, since it measures the pressure near the secretion collection container. Suitable pressure sensors are known in large numbers from the prior art. The control device can be provided with operating elements, e.g. operating buttons and/or a display, in particular a touchscreen display. It can be mains-operated but is preferably provided with an autonomous power source, e.g. in the form of disposable or rechargeable batteries. This allows the device to be made portable. The control device can comprise a memory, e.g. a flash memory, and can be configured to store predetermined operating data in the memory, either continuously or at defined times, in particular the pressure measured in the secretion collection container and/or the operating state of the vent valve. Thus, for example, the times at which the vent valve is opened and closed can be stored. It is possible in this way for the healing process of the patient to be monitored.

In addition, the device can be provided with a flow sensor in order to measure the volumetric flow of gas entering the device from the secretion collection container through the container connector. The control device is then preferably configured to display the measured volumetric flow of gas and/or to store this in the memory continuously or at defined times. This permits still better monitoring of the healing process.

The device can be configured in such a way that an active operation is optionally enabled, i.e. a vacuum can optionally be applied to the secretion collection container. For this purpose, the device can comprise a vacuum connector for connection to a vacuum source. The latter is preferably an external vacuum source, e.g. a hospital vacuum system, such that the actual device can be kept very compact. However, the device itself can also comprise an internal vacuum source, e.g. a suction pump. With a vacuum connector present, it is possible, when so required, to treat patients initially using active thoracic drainage (e.g. in an initial phase after surgery) and, when the course of healing has progressed, to switch to passive thoracic drainage without changing the drainage device. It is also possible, if appropriate, for a switch to be made the other way round, that is to say from passive operation to active operation, should this prove necessary. Given the absence of a water seal, the device can be run with very little noise in active operation, whereas, when a water seal is present, there is a (frequently annoying) bubbling sound as air escapes.

For this purpose, between the container connector and the vacuum connector, a controllable second valve is preferably provided which can be selectively opened such that a vacuum present at the vacuum connector can be applied to the secretion collection container. This valve is also designated hereinbelow as a vacuum valve. The switching between passive operation and active operation can thus be performed automatically by the control device on the basis of predetermined criteria.

The device can further comprise a second pressure sensor, which is configured to measure the pressure at the vacuum connector. This pressure sensor is also designated hereinbelow as a vacuum pressure sensor. The control device can then monitor the pressure measured by the second pressure sensor. The control device can be configured in such a way that it automatically opens the second valve only when the pressure at the vacuum connector is negative in relation to the atmospheric pressure and/or falls below a defined limit value. If appropriate, however, it opens the second valve only when further conditions are met, e.g. when the first pressure sensor, or a patient sensor to be described in more detail below, indicates a positive pressure or too small a negative pressure in the pleural cavity, which points to the need for active aspiration.

The control device can be configured to visually display the measured values of the second pressure sensor and/or the operating position of the second valve, and/or to store the measured values of the second pressure sensor and/or the operating position of the second valve in the memory of the control device, either continuously or at defined times, in order to ensure improved patient monitoring.

The second valve can be configured as a servo valve (control valve), which not only can adopt two states (closed/opened) but has a substantially continuously adjustable opening cross section and is thus suitable for substantially continuously adjusting the vacuum pressure applied to the secretion collection container. It is thus possible for the control device to actively regulate the vacuum pressure applied to the secretion collection container and, in consequence, to the pleural cavity. To regulate the vacuum pressure, the control device can in particular use the pressure values measured by the container pressure sensor or by a patient pressure sensor, which is described in more detail below. The optional flow meter is preferably arranged between the container connector and the vacuum valve, such that the volumetric flow generated by the vacuum can be measured.

Specifically, the arrangement of the valves and sensors is preferably chosen as follows: A vent line leads from the container connector to the atmosphere. The first valve (vent valve) is arranged in this line, and the first pressure sensor (container pressure sensor) measures the pressure in this line between the container connector and the vent valve. The optional flow sensor is likewise arranged in this line between the container connector and the vent valve. Moreover, a vacuum line, which leads to the vacuum connector, preferably branches off from the vent line between the container connector and the vent valve. This line preferably has a smaller cross section than the vent line, in order to limit the maximum possible suction power. The second valve (vacuum valve) and the second pressure sensor (vacuum sensor) are, if present, arranged in or on this line. In this way, the applied vacuum can be controlled or regulated completely independently of the above-described control of the vent valve, and the vent valve remains permanently closed in the active operating mode. The vacuum line preferably branches off from the vent line only downstream of the flow sensor. In this way, the flow can be measured, and if appropriate recorded, also in the active operating mode.

Optionally, the device can further comprise a filling level sensor for measuring the filling level (i.e. the accumulated quantity of secretion) present in the secretion collection container. This can in particular be a capacitive sensor, which is mounted on a wall of the device facing towards the secretion collection container. This sensor can likewise be connected to the control device. The control device is then preferably configured to output a signal when the liquid level exceeds a predetermined value. The control device can alternatively or additionally be configured to visually indicate the liquid level, e.g. on a scale or in another suitable manner in a display of the control device, and/or to store the measured liquid level in the memory either continuously or at defined times.

Thoracic drainage procedures are nowadays performed in most cases using a twin-hose system. A first hose serves as drainage line, in order to convey air and secretions from the catheter to the secretion collection container. A second hose serves as ancillary line. This ancillary line opens at the patient-side (proximal) end into the drainage line. The ancillary line then generally serves to measure the pressure in the pleural cavity, without this measurement being falsified by siphon effects in the drainage line. In addition, the ancillary line can be used to flush the drainage line if blockages occur in the drainage line.

For use with a twin-hose system, the device, in addition to comprising the container connector, can also comprise a connector for an ancillary line of this kind. A third pressure sensor is then connected to this connector. This pressure sensor is also designated hereinbelow as patient pressure sensor, because it permits measurement of the actual pressure conditions in the pleural cavity of the patient. This pressure sensor is then preferably connected in turn to the control device. The control device can in turn store and/or display the pressure values, measured by this sensor, continuously or at defined times. The control device preferably monitors the pressure values measured by the patient pressure sensor and compares these values continuously, or at defined times, with the pressure values measured by the container pressure sensor. If these values deviate from one another by more than a predefined amount, this indicates a blockage of the drainage line, and the control device can output a corresponding signal. This signal can serve in particular to trigger an automatic flushing procedure. As has already been mentioned, the patient pressure sensor can also be used to regulate the vacuum pressure in the pleural cavity.

The connector for the ancillary line is preferably connected to a third controllable valve, which is designated hereinbelow as flushing valve. In the closed state, this valve closes off the connector for the ancillary line from the atmosphere at the device end. If a vacuum connector is present, the flushing procedure can then be carried out as follows. The control device opens the flushing valve on the one hand and the vacuum valve on the other hand. This creates a vacuum in the drainage line and therefore also in the ancillary line. This has the effect that air from the atmosphere is sucked through the flushing valve into the ancillary line and passes through the drainage line to the vacuum source. The drainage line is flushed in this way, as is also explained in principle in, for example, WO 2005/061025.

The valves mentioned, the sensors mentioned and the control device are preferably accommodated in a common housing. The secretion collection container can preferably be connected releasably to this housing, e.g. via a snap-fit connection. A connector part, which can be mounted releasably on the housing, can also be provided for the attachment of the drainage line and of the optional ancillary line. The connection between the drainage line or ancillary line and the secretion collection container or housing can be configured in accordance with WO 2007/128156 or WO 2008/141471, for example, the complete disclosure of which documents in this respect is incorporated herein. All of this therefore results in a compact system that can be produced inexpensively and that can be configured to be portable. Depending on requirements, different sizes of secretion collection containers can be coupled to the housing. The secretion collection containers, which are preferably disposable, can be exchanged easily and in a way that does not inconvenience the patient.

The control device preferably has a digital processor, and a memory in which a computer program is stored, which computer program, when executed by the processor, has the effect that the control device performs the abovementioned steps.

Thus, in a second aspect, the present invention also relates to a computer program. A computer program is thus proposed for controlling a thoracic drainage device with a secretion collection container, at least one controllable first valve, at least one first pressure sensor, and a control device cooperating with the first valve and with the first pressure sensor, wherein the computer program, when executed, causes the control device to carry out the following steps:

reading out the first pressure sensor in order to determine a pressure in the secretion collection container; and controlling the first valve in order to release air from the secretion collection container when the determined pressure exceeds a first threshold value.

If a vacuum connector is present, the computer program, when executed, preferably further causes the control device to carry out the following steps:

determining a difference between a pressure at a vacuum connector of the thoracic drainage device and atmospheric pressure;

automatically opening a controllable second valve, arranged between the secretion container and the vacuum connector, when said difference falls below a predetermined limit value and, optionally, further criteria are met.

Finally, if a patient pressure sensor and a flushing valve are also present, as has been described above, the computer program, when executed, can cause the control device to carry out the abovementioned flushing procedure.

Further refinements of the computer program are set forth in the dependent claims. Such refinements also derive analogously from the above considerations concerning the device.

The computer program can be present in particular in the form of a computer program product on a suitable data carrier, e.g. on a CD-ROM, on a flash memory, etc., or can be provided for download via a network. It can be present in any desired form, e.g. as source code, object code or machine code.

In a third aspect, the present invention also relates to a method for operating a thoracic drainage device with a secretion collection container, said method comprising the following steps:

determining a pressure in the secretion collection container;

releasing air from the secretion collection container by means of a controllable valve when the pressure exceeds a first threshold value.

The method can further comprise:

determining the difference between the pressure at a vacuum connector of the thoracic drainage device and the atmospheric pressure;

automatically opening a controllable second valve, arranged between the secretion container and the vacuum connector, when said difference falls below a predetermined limit value and, optionally, further criteria are met.

The method can further comprise the flushing procedure already described above.

Further refinements of this method likewise derive analogously from the above considerations concerning the device.

BRIEF DESCRIPTION OF THE DRAWINGS

Preferred embodiments of the invention are described below with reference to the drawings, which are provided only for illustrative purposes and are not to be interpreted as limiting the invention. In the drawings:

FIG. 1 shows a schematic diagram of a preferred illustrative embodiment of the present invention;

FIG. 2 shows a schematic view of a control device;

FIG. 3 shows a schematic view of a drainage device according to the invention with a first, small secretion collection container;

FIG. 4 shows a variant of the drainage device from FIG. 3;

FIG. 5 shows a schematic view of a drainage device according to the invention with a second, larger secretion collection container;

DESCRIPTION OF PREFERRED EMBODIMENTS

Figure 6:
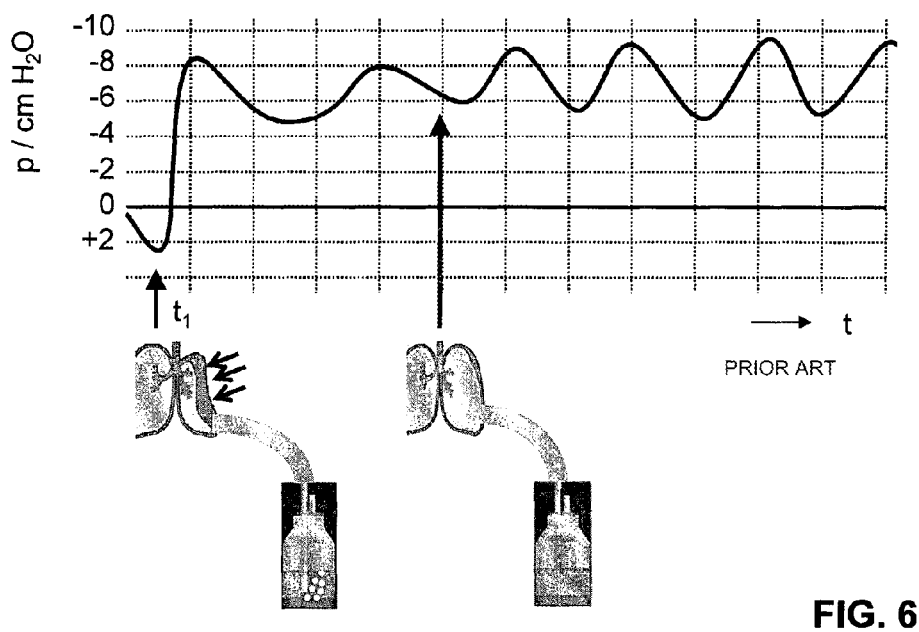
FIG. 6 shows a diagram representing a typical time profile of the pleural pressure when using a thoracic drainage device of the prior art.

FIG. 1 is a schematic diagram of a thoracic drainage device 100 according to the invention. The pleural cavity 1 of a patient is connected to a secretion collection container 3 via a drainage catheter (not shown) and via a drainage line 2 attached to said drainage catheter. This secretion collection container 3 is used to separate liquid and gaseous constituents. The liquid secretions 4 collect at the bottom of the secretion collection container 3, while the gaseous constituents (principally air) pass through a filter 5 and via a container connector 16 into a vent line 13. First a flow sensor 6 and then an electrically controllable vent valve 12 are arranged in succession in the vent line 13, as seen in the direction of flow 14. In the opened state, the vent valve 12 frees the vent line 13 to the atmosphere at an outlet 15. A container pressure sensor 11 measures the pressure between the flow sensor 6 and the vent valve 12. This pressure sensor can also be arranged upstream of the flow sensor 6, e.g. directly at the container connector 16. The container pressure sensor 11 and the vent valve 12 together form an air release unit (venting unit) 10. A control device 7 with memory 8 reads out the signals from the sensors 6 and 11 and controls the valve 12.

In normal passive operation, air and secretions from the pleural cavity 1 pass through the drainage line 2 into the secretion collection container 3. To ensure that the air can escape from the secretion collection container 3 without appreciable counterpressure, the control device 7 measures, by means of the container pressure sensor 11, the pressure near the container connector 16 and opens the vent valve 12 as soon as this pressure is just above the atmospheric pressure. The selected response threshold at which the vent valve 12 opens can be very low. As soon as the pressure falls back below the atmospheric pressure, the control device 7 closes the vent valve 12 again. This avoids air flowing back into the pleural cavity 1. Thus, the air release unit 10 and the control unit 7 together form what is basically an electronic nonreturn valve with a very low response threshold.

In this example, an optional filling level sensor 9 is present which, for example, capacitively determines the filling level of the secretion collection container 3 and forwards it to the control unit 7. In this way, the patient or the medical personnel can be alerted in good time, for example by a visual or acoustic alarm signal, when the secretion collection container 3 is almost full.

A vacuum line 23 is optionally present, which runs from the vent line 13 to a vacuum connector 25. An electrically controllable vacuum valve 22 is arranged in the vacuum line. A vacuum sensor 21 measures the pressure between the vacuum connector 25 and the vacuum valve 22. The vacuum sensor 21 and the vacuum valve 22 form a vacuum control unit 20. For safety reasons, in order to avoid too strong a suction effect, the cross section of the vacuum line 23 is chosen to be smaller than that of the vent line 13.

The vacuum sensor 21 and the vacuum valve 22 are also connected to the control device 7. The latter establishes whether a vacuum is in fact needed by the patient, i.e. whether the drainage device 100 should indeed be operated in the active mode. This can be established, for example, by manual input by the medical personnel, for example if the medical personnel observe an air fistula that should be treated by an active operation. However, a change between the passive operating mode and the active operating mode can also be carried out automatically by the control device 7, for example if the pressure measured by the container pressure sensor 11, or by the patient pressure sensor 31 described below, is very close to the atmospheric pressure over an extended period of time.

If an active operation is wanted, the control device 7 determines, with the vacuum sensor 21, whether a sufficient vacuum is in fact present at the vacuum connector 25. The vacuum sensor 21 does not need to be particularly precise in this respect. If this is not the case, the control device 7 outputs a corresponding alarm signal, for example a visual or acoustic signal. Otherwise, the control device 7 opens the vacuum valve 22.

The control device 7 can be configured such that, with the aid of the container pressure sensor 11 and/or of the patient pressure sensor 31 described below, it automatically regulates the pressure in the secretion collection container 3 or in the pleural cavity 1 to a previously set value. Since the vacuum line 23 only branches off from the vent line 13 at a point downstream of the flow sensor 6 with respect to the direction of flow 24, the control device 7 can also continuously measure the flow in the active operating mode. The measured flow values can be used for switching back automatically to passive operation, e.g. when the flow values remain very low over an extended period of time.

A monitoring and flushing device 30 is also optionally present, which is connected via a flushing line 33, a bacterial filter 37, an ancillary connector 36 and an ancillary line 2' to the drainage catheter and, in this way, to the pleural cavity 1. The monitoring and flushing device 30 comprises a flushing valve 32 which, in the closed state, closes off the flushing line 33 from the atmosphere with which the flushing line 33 otherwise communicates via an inlet 35. A patient pressure sensor 31 measures the pressure in the flushing line 33 between the ancillary connector 36 and the flushing valve 32. The patient pressure sensor 31 and the flushing valve 32 are in turn connected to the control device 7. The control device 7 measures, with the patient pressure sensor 31, the pressure in the pleural cavity 1. In the active operating mode, the control device 7 uses these pressure values, where appropriate, to regulate the vacuum pressure. At the same time, the control device 7 periodically compares the pressure values determined by the patient pressure sensor 31 with the pressure values determined by the container pressure sensor 11. If these deviate markedly from each other, this indicates a malfunction, and the control device outputs a corresponding alarm signal. In the active operating mode, the control device can additionally trigger a flushing operation. On the one hand, the flushing valve 32 is opened for this purpose. On the other hand, the vacuum valve 22 is opened wide. In this way, air is sucked through the ancillary line 2' into the drainage line 2 and removes any blockages present in the latter.

All of the measured values determined by the control device 7 and all of the operating states can be stored by the control device in the memory 8, either continuously or at defined times. In this way, the healing process can be monitored seamlessly. In particular, the complete profile of the volumetric air flow can be recorded both in the active operating mode and also in the passive operating mode, as also can the profile of the recorded amount of secretion and all of the alarm states.

Since the device itself does not require a pump assembly, it can be made very compact and requires only minimal energy. It can therefore easily be powered by batteries over quite a long period of time. Because of the small number and low complexity of the structural parts required, the device can also be produced very inexpensively. Since no water seal and no pump assembly are present, the device runs very quietly.

FIG. 2 illustrates one possible specific design of a digital control unit 7. The control unit 7 comprises a circuit board 71, on which batteries 72, a processor 73 with integrated memory, operating elements 74 in the form of keys and a visual display device in the form of a display 75 are mounted. Analog-digital converters (ADCs), not shown here, are also provided, in order to convert the analog output signals of the various sensors into digital input signals for the processor 73, and also drive circuits for controlling the valves. The memory stores a program which, when executed in the processor, causes the control device 7 to perform the abovementioned procedures.

FIGS. 3-5 illustrate possible housing designs of a device according to the invention. The device 100 in FIGS. 3-5 comprises a housing 101, on the front face of which an on/off switch 102, operating elements 103 and a display 104 are present. A connector part 110, with which the respective device-side (distal) ends of a drainage line 2 and of an ancillary line 2' are connected, is mounted on the top face. A secretion collection container 120, which has an receiving volume of ca. 0.3 liter in the example in FIGS. 3 and 4, is clicked onto the rear face of the housing 101. However, as is shown in FIG. 5, it is also possible instead to attach a larger secretion collection container 121, e.g. with a receiving volume of 0.8 liter. The connector part 110 connects the drainage line 2 to the secretion collection container 120, while it connects the ancillary line 2' directly to the corresponding components in the device 100. A vacuum connector 25, for attachment to an in-house vacuum of a hospital or to an external vacuum pump, is formed in a side wall (FIGS. 3 and 5) or in the front face (FIG. 4).

Figure 7:
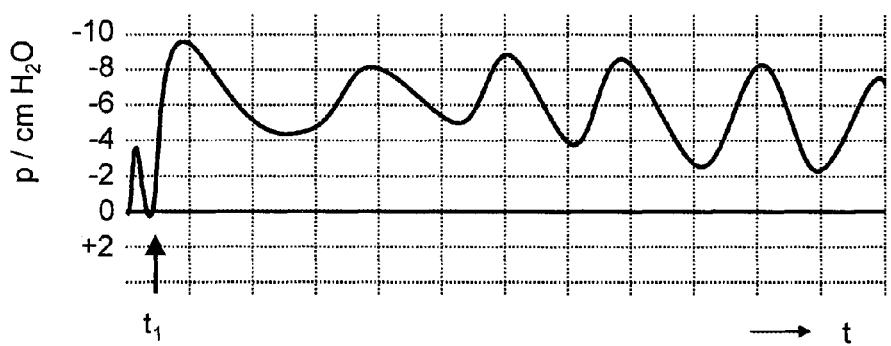
FIG. 7 shows a diagram representing a typical time profile of the pleural pressure when using a thoracic drainage device according to the invention.

FIGS. 6 and 7 illustrate a comparison of the pressure profile in the pleural cavity using a traditional passive thoracic drainage device with a water seal (FIG. 6) and using a thoracic drainage device according to the present invention (FIG. 7).

In the traditional thoracic drainage device (FIG. 6), the patient first of all has to overcome the water column in the inlet pipe of the water seal at the time $t_1$ in order to force air out of the pleural cavity, e.g. by coughing. To do this, a positive counterpressure is necessary, in this case of ca. 2 mm $H_2O$ (0.2 kPa) (illustration at bottom left of FIG. 6). This leads to a partial collapse of the lung and is not beneficial to healing. At a later time $t_2$, the pressure in the pleural cavity then once again has negative values relative to the atmospheric pressure, which values are typically between −0.5 kPa and −0.8 kPa depending on the phase of respiration (inhalation/exhalation). This is reflected by a positive water column in the inlet pipe of the water seal (illustration at bottom centre of FIG. 6).

By contrast, in the thoracic drainage device according to the present invention, the electronic one-way valve already responds at a very low positive pressure relative to the atmospheric pressure. In this way, a significant counterpressure is never built up. The patient can therefore force air out of the pleural cavity with ease, without collapsing the lung any more than is necessary.

What is claimed is:

1. A device for thoracic drainage, comprising:
    a container connector for a secretion collection container that is adapted to be connected to the pleural cavity of a patient;
    a vent line leading from the container connector to the atmosphere;
    a venting device with a controllable first valve being arranged in the vent line for releasing air from the secretion collection container and with a first pressure sensor for measuring a pressure in the secretion collection container; and
    a control device, which cooperates with the first pressure sensor and which is configured to open the first valve when a difference between a pressure in the secretion collection container and atmospheric pressure exceeds a positive first threshold value,
    wherein the first pressure sensor measures the pressure in the vent line between the container connector and the first valve.

2. The device according to claim 1, wherein the first threshold value is between 0.001 and 0.05 kPa.

3. The device according to claim 2, wherein the control device comprises a memory and is configured to store predetermined operating data in the memory.

4. The device according to claim 1, further comprising a flow configured to measure a volumetric flow of gas entering through the container connector.

5. The device according to claim 1, further comprising a vacuum connector for connection to a vacuum source.

6. The device according to claim 5, comprising a controllable second valve between the container connector and the vacuum connector in order to selectively apply a vacuum to the secretion collection container.

7. The device according to claim 5, further comprising a second pressure sensor, which is configured to measure a pressure at the vacuum connector.

8. The device according to claim 6, wherein the control device is configured to automatically open the second valve when a difference between a pressure at the vacuum connector and atmospheric pressure falls below a predetermined limit value.

9. The device according to claim 1, further comprising a connector for an ancillary line and, connected to the connector for the ancillary line, a third pressure sensor.

10. The device according to claim 9, further comprising a controllable third valve, which is connected to the connector for the ancillary line and by means of which, in the closed state, the connector for the ancillary line is closed off with respect to the atmosphere.

11. The device according to claim 1, comprising a housing in which the venting device is accommodated and which is configured to releasably connect to a secretion collection container.

12. A non-transitory computer readable medium having a set of computer executable instructions stored thereon for controlling a thoracic drainage device, the thoracic drainage device comprising a secretion collection container having a container connector that is adapted to be connected to the pleural cavity of a patient, a vent line leading from the container connector to the atmosphere, at least one controllable first valve being arranged in the vent line, at least one first pressure sensor, and a control device, the computer executable instructions comprising instructions for causing the control device to carry out the following steps:

reading out the first pressure sensor in order to determine a pressure in the secretion collection container; and controlling the first valve in order to release air from the secretion collection container when a difference between the determined pressure in the secretion collection container and atmospheric pressure exceeds a positive first threshold value;

wherein the first pressure sensor measures the pressure in the vent line between the container connector and the first valve.

13. The non-transitory computer readable medium according to claim 12, wherein the set of computer executable instructions further include instructions for causing the control device to additionally carry out the following steps:

determining the difference between a pressure at a vacuum connector of the thoracic drainage device and atmospheric pressure;

automatically opening a controllable second valve, arranged between the secretion container and the vacuum connector, when said difference falls below a predetermined limit value.

14. A method for operating a thoracic drainage device with a secretion collection container having a container connector that is adapted to be connected to the pleural cavity of a patient and with a vent line leading from the container connector to the atmosphere, said method comprising the following steps:

determining a pressure in the secretion collection container;

selectively releasing air from the secretion collection container by means of a controllable first valve being arranged in the vent line when a difference between the pressure in the secretion collection container and atmospheric pressure exceeds a positive first threshold value;

wherein the pressure is measured in the vent line between the container connector and the first valve.

15. The method according to claim 14, which method further comprises:

determining the difference between the pressure at a vacuum connector of the thoracic drainage device and the atmospheric pressure;

automatically opening a controllable second valve, arranged between the secretion container and the vacuum connector, when said difference falls below a predetermined limit value.

16. The device according to claim 3, wherein the operating data include at least one of a pressure measured in the secretion collection container and an operating state of the first valve.

17. The device according to claim 8, wherein the control device is configured to open the second valve only if further criteria are met.

18. The device according to claim 1, further comprising a flow sensor, which is arranged in the vent line between the container connector and the first valve.

19. The device according to claim 1, further comprising a vacuum line, which leads to a vacuum connector and branches off from the vent line between the container connector and the first valve.

20. The device according to claim 19, wherein at least one of a controllable second valve and a second sensor are arranged in the vacuum line.

21. The device according to claim 19, wherein the vacuum line has a smaller cross section than the vent line.

22. The device according to claim 11, wherein the housing is releasably connected to the secretion collection container of a capacity of one of 0.3 liters or larger than 0.3 liters.

23. The non-transitory computer readable medium according to claim 13, wherein the set of computer executable instructions further include instructions for causing the step of automatically opening the controllable second valve to occur when further criteria are met.

24. The method according to claim 15, wherein the step of automatically opening the controllable second valve occurs when further criteria are met.

* * * * *

UNITED STATES PATENT AND TRADEMARK OFFICE
CERTIFICATE OF CORRECTION

PATENT NO. : 9,839,726 B2
APPLICATION NO. : 14/128041
DATED : December 12, 2017
INVENTOR(S) : Hilmar Ehlert It is certified that error appears in the above-identified patent and that said Letters Patent is hereby corrected as shown below:

In the Claims

At Column 10, Line 31, "flow configured" should be -- flow sensor configured --.

Signed and Sealed this
Twenty-fourth Day of July, 2018

Andrei Iancu
*Director of the United States Patent and Trademark Office*